United States Patent [19]

Padovan et al.

[11] 4,113,769

[45] Sep. 12, 1978

[54] PROCESS FOR PREPARING UNSATURATED CARBOXYLIC ACIDS BY GAS PHASE CATALYTIC OXIDATION OF THE CORRESPONDING ALDEHYDES

[75] Inventors: Mario Padovan, Milan; Giordano De Alberti, Besnate; Giancarlo Battiston, Baranzate; Romano Covini, Milan, all of Italy

[73] Assignee: Montedison S.p.A., Milan, Italy

[21] Appl. No.: 734,248

[22] Filed: Oct. 20, 1976

[30] Foreign Application Priority Data

Oct. 23, 1975 [IT]  Italy ............................... 28606 A/75

[51] Int. Cl.$^2$ ............................................. C07C 51/32
[52] U.S. Cl. ................................. 562/534; 252/443; 252/455 R; 252/456; 252/464; 252/470
[58] Field of Search ................... 260/530 N; 252/470, 252/456, 455 R, 464, 443

[56] References Cited

U.S. PATENT DOCUMENTS

| 3,775,474 | 11/1973 | O'Hara et al. | 260/530 N |
|---|---|---|---|
| 3,875,220 | 4/1975 | White et al. | 260/530 N |
| 3,997,600 | 12/1976 | Ferlazzo et al. | 260/530 N |

*Primary Examiner*—Vivian Garner

*Attorney, Agent, or Firm*—Stevens, Davis, Miller & Mosher

[57] ABSTRACT

A process is disclosed for preparing acrylic acid or methacrylic acid comprising reacting in vapor phase acrolein or methacrolein (respectively) with molecular oxygen or an oxygen-containing gas, at a temperature between 200° and 350° C, in the presence of a solid catalyst, and with a contact time between 0.5 and 5 seconds, characterized in that the solid catalyst comprises molybdenum, vanadium, tungsten, cobalt, chromium and oxgyen chemically combined with these elements, the atomic ratios among the aforesaid elements being represented by the empirical formula: Mo$_{12}$V$_a$W$_b$Co$_c$Cr$_d$O$_e$, wherein:

$a$ is between 0.5 and 10,
$b$ is between 0.5 and 8,
$c$ is between 1 and 6,
$d$ is between 0.1 and 3, and
$e$ is a number sufficient to satisfy the valence requirements of the other elements;

and with the further proviso that $a+b+c$ is equal to or greater than 8.5. The catalyst is preferably used while on a carrier, and the reaction is preferably carried out in the presence of an inert gaseous diluent or water vapor.

3 Claims, No Drawings

PROCESS FOR PREPARING UNSATURATED CARBOXYLIC ACIDS BY GAS PHASE CATALYTIC OXIDATION OF THE CORRESPONDING ALDEHYDES

The present invention relates to a process for preparing certain unsaturated carboxylic acids by the catalytic oxidation in the vapor phase with molecular oxygen, or with an oxygen-containing gas, of the corresponding low molecular weight unsaturated aldehyde containing more than two carbon atoms. In its preferred embodiment, the invention is particularly useful in the production of acrylic acid from acrolein. Methacrylic acid may also be produced from methacrolein in similar fashion.

The process according to the present invention is characterized in that the low molecular weight unsaturated aldehyde is oxidized in the presence of a catalyst composed of, or consisting essentially of, molybdenum, vanadium, tungsten, cobalt, chromium and, furthermore, of oxygen chemically combined with the above-mentioned elements.

The relative atomic ratios of the elements in the catalyst according to this invention correspond to the following empirical formula:

$$Mo_{12}V_aW_bCo_cCr_dO_e$$

wherein:
 $a$ is between 0.5 and 10,
 $b$ is between 0.5 and 8,
 $c$ is between 1 and 6,
 $d$ is between 0.1 and 3, and
 $e$ is a number sufficient to satisfy the valence requirements of the other elements, and
with the further provision that $a+b+c$ is equal to or greater than 8.5 for every 12 atoms of molybdenum.

The empirical formula above merely indicates the atomic ratios in which the various elements are present in the catalyst composition, independently of the type of chemical bond or bonds actually existing amongst the several elements.

It has already been suggested to oxidize unsaturated aldehydes to the corresponding unsaturated acids over catalysts composed of Mo, V, W, O.

It has now been found in accordance with the present invention, that by adding Co and Cr to the previous Mo, V, W, O catalyst system, it becomes possible to unexpectedly improve the catalyst efficiency. The extent of such improvement clearly appears from a comparison between the results of Examples 1 to 4 below and those of the last three Examples 5 to 7.

The catalyst may be employed without a carrier, or with a suitable carrier such as, for example, silica, alumina, silica-alumina, silicon carbide, pumice, etc.

Various processes well known per se in the prior art can be used to prepare the catalyst. More particularly, one may mix in an aqueous medium compounds of the various desired elements and then successively evaporate the suspension thereby obtained with or without the optional addition of a carrier.

The combination of the various desired elements constituting the catalyst — no matter how obtained — is then subjected to calcining in an air stream at a temperature ranging from 330° to 470° C for a time period of at least 2 hours.

The process of the present invention may be practised in any type of reactor suitable for carrying out oxidations in the gas phase. One may utilize either fixed bed or fluid bed reactors as desired.

The reaction temperature for the desired conversion of the low molecular weight unsaturated aldehyde ranges from 200° to 350° C.

The reaction can be conducted at normal atmospheric pressure or under superatmospheric pressures, for instance up to 10 atmospheres.

The contact time, defined as the ratio between the apparent volume of the catalyst and the volume of the gas fed under the reaction conditions per unit of time is between 0.5 and 5 seconds.

The concentration of the low molecular weight unsaturated aldehyde is preferably between 2.5 and 8.5% by volume in respect of the feed mixture. The molar ratio between the oxygen and the unsaturated aldehyde preferably ranges from 0.5 to 6. The oxygen necessary for the oxidation step can be introduced in the pure or substantially pure state. However, if there are no particular reasons for any particular concentration, the preferred oxidizing agent is ordinary atmospheric air.

The oxidation is preferably conducted in the presence of one or more diluents, such as nitrogen, carbon dioxide, water vapor, etc. Of the numerous possible diluents, water vapor is particularly well suited. The water vapor concentration is preferably between 20 and 50% in respect of the feed mixture.

The following examples are given with a view of still better illustrating the invention, without however being any limitation thereon.

The terms "conversion" and "selectivity" used herein have the following meanings:

$$\text{aldehyde conversion in \%} = \frac{\text{moles of fed aldehyde} - \text{moles of unreacted aldehyde}}{\text{moles of fed aldehyde}}$$

$$\text{selectivity to product in \%} = \frac{\text{gram atoms of carbon in the product}}{\text{gram atoms of carbon in the reacted aldehyde}}$$

EXAMPLE 1

A catalyst of composition $Mo_{12}V_{4.9}W_{2.6}Co_{4.8}Cr_{0.6}O_e$ was prepared as follows:

76.1 g of $(NH_4)_2Mo_2O_7$, 21.5 g of $NH_4VO_3$, 25.7 g of $(NH_4)_6H_2W_{12}O_{40}\cdot nH_2O$ (ammonium tungstate at 90% of $WO_3$), and 3 g of $(NH_4)_2Cr_2O_7$ were dissolved, with stirring and heating, in 1250 cc of deionized water. The solution was brought to 70° C and 51.75 g of $Co(NO_3)_2\cdot 6H_2O$ dissolved in 75 cc of water were admixed therewith.

Under stirring, the mixture was then evaporated to dryness on a water bath. After drying in an oven at 120° C, the residue was calcined at 400° C for 5 hours in an air stream. The product of calcination was ground and the fraction between 60 and 80 mesh (Tyler series) was collected and used as the catalyst.

7 ml of the catalyst were placed in the form of a fixed bed in a steel reactor having a diameter of 10 mm, thermoregulated in a conventional molten salts bath. A gaseous mixture consisting of 7.5% of acrolein, 57.5% of air, and 35% of steam was passed through the catalyst at a space velocity corresponding to a contact time of 2 seconds, and at a temperature of 320° C.

The following results were obtained:
conversion of acrolein : 98.7%
selectivity to acrylic acid : 91.3%.

EXAMPLES 2 to 7

Following the procedure of Example 1, catalysts having the compositions reported in the following table were prepared:

Acrolein was oxidized in the presence of these catalysts as described in Example 1, at the respective temperatures and contact times indicated in the table.

TABLE

| Example No. | Catalytic composition | Reaction Temperature °C | Contact time sec. | Acrolein conversion % | Selectivity to acrylic acid % |
|---|---|---|---|---|---|
| 2 | $Mo_{12}V_2W_4Co_{4.8}Cr_{0.6}O_e$ | 300° | 2 | 98.1 | 93.4 |
| 3 | $Mo_{12}V_2W_4Co_4Cr_{0.6}O_e$ | 280° | 2 | 96.3 | 90.1 |
| 4 | $Mo_{12}V_{4.8}W_3Co_1Cr_{0.6}O_e$ | 300° | 2 | 99.0 | 85.2 |
| 5 | $Mo_{12}V_2W_{2.4}O_e$ | 280° | 2 | 99.6 | 76.3 |
| 6 | $Mo_{12}V_{4.6}W_{2.4}O_e$ | 260° | 2 | 97.8 | 80.6 |
| 7 | $Mo_{12}V_6W_{2.4}O_e$ | 280° | 2 | 84.8 | 68.1 |

What is claimed is:

1. A process for preparing acrylic acid or methacrylic acid comprising reacting in vapor phase acrolein or methacrolein with molecular oxygen or an oxygen-containing gas, at a temperature between 200° and 350° C, in the presence of a solid catalyst, and with a contact time between 0.5 and 5 seconds, characterized in that the solid catalyst consists essentially of molybdenum, vanadium, tungsten, cobalt, chromium and oxygen chemically combined with these elements, the atomic ratios amongst the aforesaid elements being represented by the empirical formula: $Mo_{12}V_aW_bCo_cCr_dO_e$, wherein:

$a$ is between 0.5 and 10,
$b$ is between 0.5 and 8,
$c$ is between 1 and 6,
$d$ is between 0.1 and 3, and
$e$ is a number sufficient to satisfy the valence requirements of the other elements;

and with the further proviso that $a+b+c$ is equal to or greater than 8.5.

2. A process according to claim 1, in which the catalyst is used while on a carrier.

3. A process according to claim 1, in which the reaction is carried out in the presence of an inert gaseous diluent or water vapor.

* * * * *